United States Patent [19]
Jung

[11] Patent Number: 6,108,581
[45] Date of Patent: Aug. 22, 2000

[54] FAR INFRARED RAY DIFFUSING MAT

[76] Inventor: Yeon-Kweon Jung, 908-903, Dongsin Apt., Imae-dong, Pundang-gu, Seongnam-city, Kyungki-do, Rep. of Korea

[21] Appl. No.: 09/152,374

[22] Filed: Sep. 14, 1998

[30] Foreign Application Priority Data

May 30, 1998 [KR] Rep. of Korea ..................... 98-9186

[51] Int. Cl.[7] ................................. A61F 2/00; A61N 1/00
[52] U.S. Cl. .......................... 607/100; 607/98; 607/115; 607/96
[58] Field of Search ............................. 607/96, 100, 98, 607/3, 103, 115; 606/32

[56] References Cited

U.S. PATENT DOCUMENTS

| | | |
|---|---|---|
| 1,589,338 | 6/1926 | White . |
| 2,323,478 | 7/1943 | Lobl ......................................... 219/46 |
| 3,045,100 | 7/1962 | Mills ........................................ 219/34 |
| 3,089,033 | 5/1963 | Fujisawa ................................... 250/88 |
| 4,186,294 | 1/1980 | Bender .................................... 219/527 |
| 4,303,074 | 12/1981 | Bender .................................... 128/399 |
| 4,680,822 | 7/1987 | Fujino et al. ............................... 5/421 |
| 4,777,346 | 10/1988 | Swanton, Jr. ............................. 219/313 |
| 4,825,868 | 5/1989 | Susa et al. ................................ 128/376 |
| 4,888,972 | 12/1989 | Nakai et al. .............................. 250/504 |
| 5,835,983 | 11/1998 | McMahen et al. ...................... 219/527 |
| 5,944,740 | 8/1999 | Inoue et al. ................................. 607/1 |

*Primary Examiner*—Linda C. M. Dvorak
*Assistant Examiner*—Jocelyn Debra Ram
*Attorney, Agent, or Firm*—Merchant & Gould P.C.

[57] ABSTRACT

A far infrared ray diffusing mat having sequential layers of a first cushion plate with a predetermined thickness for protecting things placed above; a heat reflecting plate and a water vein blocking plate on the first cushion plate; a heating wire of many carbon fibers arranged in a zig-zag shape on the second cushion plate; an insulation coating plate on the heating wire; a plurality of crossed insertion parts sewn with double layers of textile materials at a predetermined lengthwise distance on the insulation coating plate; a far infrared ray diffusing pad positioned on the crossed insertion parts filled with mineral particles; and a third cushion plate on the far infrared ray diffusing pad, all of those layers being sequentially placed between upper and lower sheets, thereby blocking water vein and electronic waves harmful for health, generating out far infrared ray, dissolving toxic gas and forming negative ion, as the heat passes through mineral particles during heating, effective for sickness and fatigue release.

4 Claims, 3 Drawing Sheets

FAR INFRARED RAY DIFFUSING MAT

BACKGROUND OF THE INVENTION

1. Field of the Invention

The present invention relates to a mat, and more particularly to a far infrared ray diffusing mat which has sequential layers of a water vein blocking plate, an electronic wave blocking plate and a mineral particle plate on top of a conventional structure of the mat with a heating wire, thereby effectively helping a user to sleep soundly, treating illness and overcoming fatigue.

2. Description of the Prior Art

Due to the concentration of population in cities and restrictions in residential area, office-com-hotels and apartments have become more popular than private houses. Most office-com-hotels and apartments have been built with a centrally controlled and simultaneous (for all rooms) heating system for maximum reduction in cost. It is necessary for families, especially with children or old people, to keep a separate heater for the times when heating is not provided.

The conventional mat has an internal heating wire which heats when an electric switch signals heating. However, there is a problem in the conventional mat in that the heating wire is made of nicrome which generates electronic waves thereby causing negative influence on health and discomfort in sleep. Therefore, the mat has been used as a temporary alternative only when the centrally controlled heating is not provided.

SUMMARY OF THE PRESENT INVENTION

The present invention is presented to solve the aforementioned problems and it is an object of the present invention to provide a far infrared ray diffusing mat having sequential layers of a water vein blocking plate, an electronic wave blocking plate and a far infrared ray diffusing plate beneficial for sleep, treatment of sickness and release of fatigue.

In order to achieve the above mentioned object, the present invention includes:

- a first cushion plate with a predetermined thickness for protecting things placed above;
- a heat reflecting plate and a water vein blocking metal plate on the first cushion plate;
- a second cushion plate on the heat reflecting plate;
- a heating wire of many carbon fibers arranged in a zig-zag shape on the second cushion plate;
- an insulation coating plate on the heating wire;
- a far infrared ray diffusing pad disposed on the insulation coating plate, the pad having a plurality of crossed insertion parts formed by sewing double layers of textile materials in vertical and horizontal directions at a predetermined distance and filled with mineral particles therein; and
- a third cushion plate on the far infrared ray diffusing pad, all of those layers being sequentially placed between upper and lower sheets.

It is another object of the present invention to make the heat reflecting plate and the water vein blocking plate out of aluminum in a singular layer.

It is a still another object of the present invention to fill the crossed insertion parts of the far infrared ray diffusing pad with finely ground mica.

DETAILED DESCRIPTION OF THE INVENTION

Figure 1:
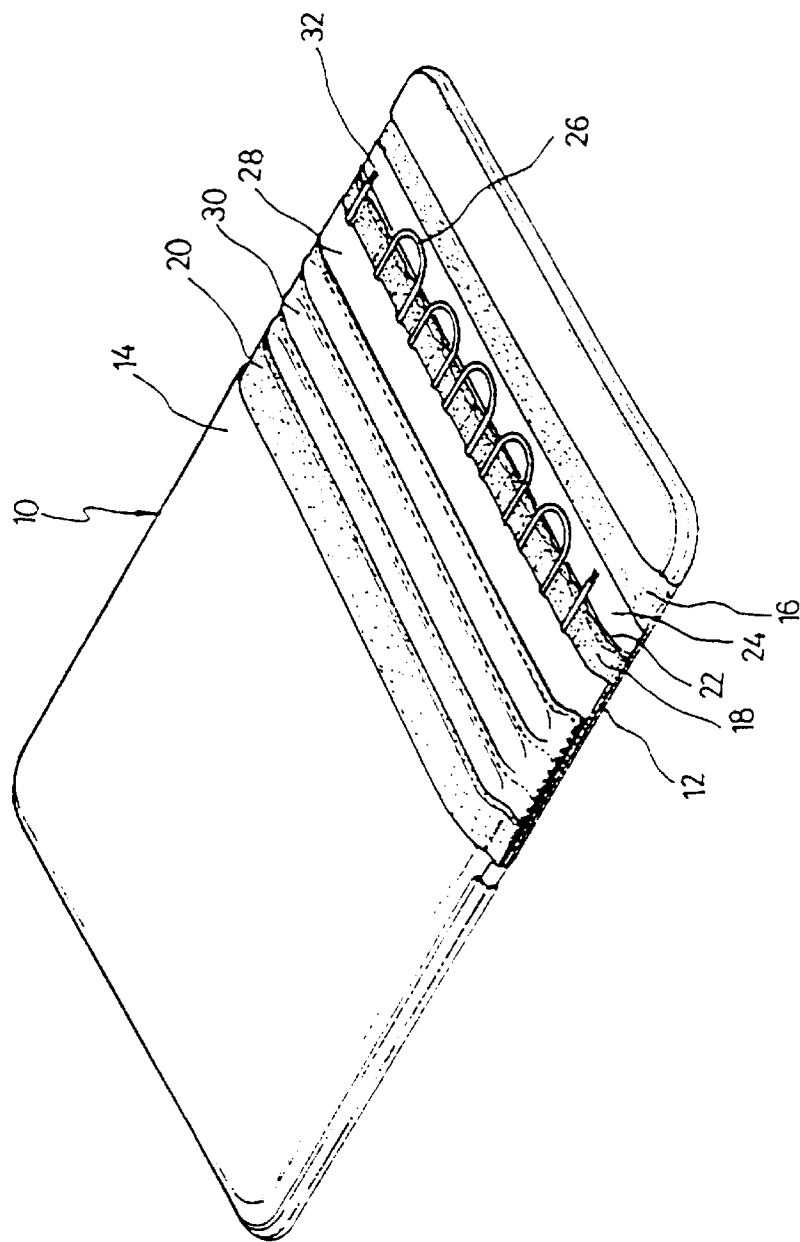
FIG. 1 is a perspective sectional view for illustrating important parts in accordance with the present invention.
Figure 2:
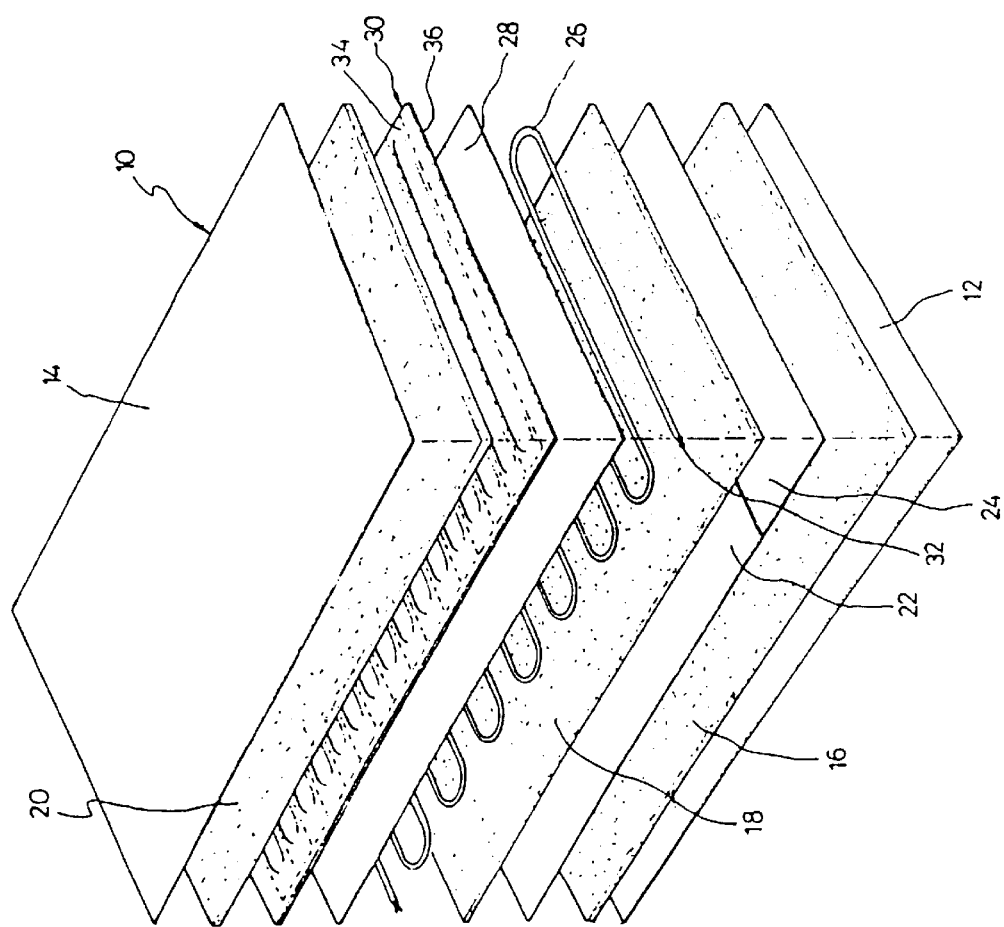
FIG. 2 is a separate perspective view of FIG. 1.
Figure 3:
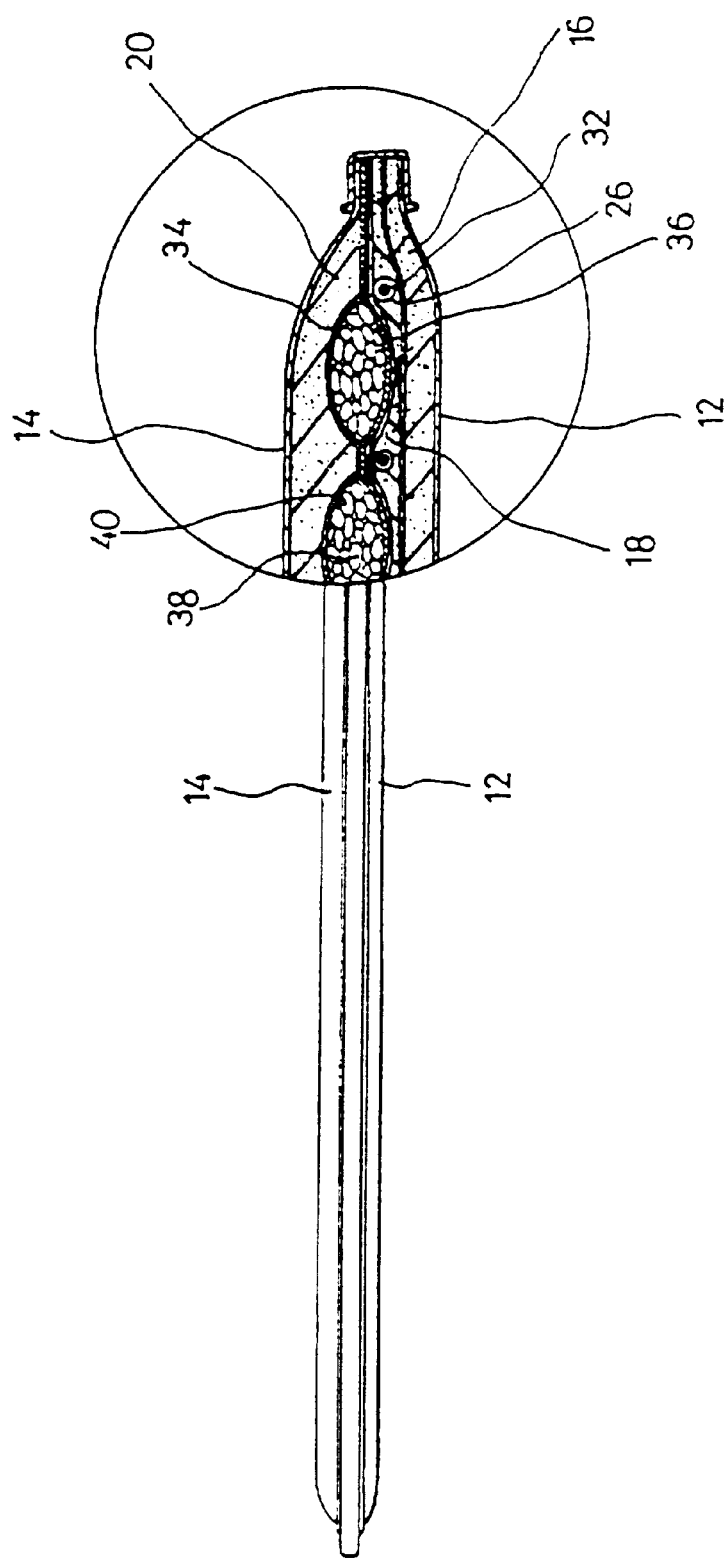
FIG. 3 is a sectional view in accordance with the present invention.

An embodiment of the present invention will be described in detail with accompanying drawings. FIG. 1 is a perspective sectional view for illustrating important parts in accordance with the present invention; FIG. 2 is a separate perspective view of FIG. 1; and FIG. 3 is a sectional view in accordance with the present invention.

The far infrared ray diffusing mat 10 of the present invention has upper and lower sheets 14 and 12 sewn to an external frame of the mat. Between the two sheets are sequential layers of the first, second and third cushion plates 16, 18 and 20, the heat reflecting plate 22 and the water vein blocking metal plate 24, the heating wire 26, the insulation coating plate 28 and the far infrared ray diffusing pad 30.

The first, second and third cushion plates 16, 18 and 20 are made of wide textile material with a predetermined thickness. Good candidates for the cushion plates are a variety of textile materials with good resilience such as cotton fibers, sponge or other foamy materials. The cushion plates should have an impact absorbing effect to safely protect the matters filled in the mat.

In other words, the first cushion plate 16, the heat reflecting plate 22 and the water vein blocking plate 24 are placed on the lower sheet 12 in a sequence. The heat reflecting plate 22 is commonly made of thinly manufactured aluminum plate for reflecting upward without loss the heat generated at the heating wire. Below the heat reflecting plate 22, the water vein blocking metal plate 24 is included to effectively restrict little vibrations generated by the water vein, underground water flow, thereby preventing harmful influence upon a human body. Though the water vein blocking plate has been commonly made of pure copper, aluminium can also be used for the same purpose in consideration of its scientifically recognized effectiveness.

In the present invention an identical material is used for making the heat reflecting plate 22 and the water vein blocking metal plate 24, so as to improve flexibility and production of the mat and to make both plates into a single layer with a predetermined thickness.

When the water vein blocking metal plate 24 and the heat reflecting plate 22 are made into two separate layers, the manufacturing cost will be higher than for a single layer but more advantageous in the effectiveness of reflecting heat because of air contained between the two plates 24 and 22, and in portability and storage because of improved flexibility.

The second cushion plate 18 is positioned on the heat reflecting plate 22. The heating wire 26 is arranged on the second cushion plate 18 in a zig-zag shape for generating and transmitting heat when a switch (not shown) is turned on/off.

The heating wire 26 is made of a plurality of carbon fibers 32 wrapped with an insulation material and used for generating and transmitting heat and the switch is turned on/off. The carbon fibers have advantageous properties such as high corrosion-resistance, low heat expansion, excellent heat conductivity and superior heat resistance, to thereby effectively block electronic waves leading to beneficial uses for health maintenance and sickness treatment.

On the heating wire 26 is the thin and flexible insulation coating plate 28. The far infrared ray diffusing pad 30 is mounted on the insulation coating pad 28 where the double layers of textile material 34 and 36 are sewn in vertical and horizontal directions on the same plane at a predetermined distance to form crossed insertion parts 40 filled with finely ground mineral particles.

At this time, finely ground mica is suitable for the mineral particles 38 because of heat retention and noise blocking effects. The finely ground mica is composed of mainly minerals like quartz and black and white mica with a small amount of feldspar, tourmaline, zircon, garnet, apatite and with a pretty large quantity of germanium, a non-transparent mineral.

It is desirable to keep the size of finely ground mica at about 8–30 mm. If the particle size is under 8 mm, its heat reflecting and diffusing effect is reduced. If the particle size is over 30 m, its heat retention is negatively affected due to excessive spaces. Yellow soil can also be substituted for the mineral particles 38.

The reasons for forming the crossed insertion parts 40 in horizontal and vertical directions on the far infrared ray diffusing pad 30 are that the mat 10 in its open state can be conveniently folded along the sewn line and that the mineral particles are restricted in the crossed insertion parts 40 without being pushed or collected at one side of the mat in spite of the user's body movements like sitting or lying.

Furthermore, the heating wire 26 is arranged in the zig-zag shape between two crossed insertion parts 40 to evenly transmit heat when the switch is on. The third cushion plate 20 of a textile material is mounted on the far infrared ray diffusing pad 30 to effectively absorb any impact and to improve resistance to any shock.

In order to use the far infrared ray diffusing mat 10, the user spreads the mat 10 on the floor and turns on the switch (not shown). The heating wire 26 generates and transmits heat in accordance with the switch signal. The heat is being generated and transmitted upward while electronic waves are blocked due to the unique property of the carbon fibers 32. At the same time, the heat transmitted downward is also reflected upward by the heat reflecting plate 22. Then, the heat passes through the mineral particles 38 filled at a predetermined distance in the far infrared ray diffusing pad 30, thereby expanding to all directions and radiating out the far infrared ray.

In addition, the water vein flowing under ground, partly recognized harmful for health in modern science, is blocked by the water vein blocking plate 24 in the mat 10, so that the user will not be influenced by it at all.

Therefore, there is an advantage of the present invention in that the far infrared ray diffusing mat has sequential layers of a heat reflecting plate, a water vein blocking plate, a heating wire, a far infrared ray diffusing pad and cushion plates therebetween, thereby blocking water vein and electronic waves harmful for health, generating out far infrared ray, as the heat passes through mineral particles during heating, (effective for sickness and fatigue release.)

There is another advantage of the present invention in that a plurality of crossed insertion parts are sewn in horizontal or vertical direction with far infrared ray diffusing pads filled with mineral particles, thereby conveniently opening and folding along the sewn line and effectively preventing the mineral particles from being collected at one side of the mat.

What is claimed is:

1. A far infrared ray diffusing mat, comprising:
    upper and lower sheets, and sequential plates and pad placed between the upper and lower sheets, said plates and pad comprising:
    a first cushion plate;
    a heat reflecting plate on the first cushion plate for reflecting far infrared rays;
    a water vein vibration-blocking metal plate adhered to one side of the heat reflecting plate;
    a second cushion plate on the heat reflecting plate;
    a heating wire of carbon fibers arranged in a zig-zag shape on the second cushion plate;
    an insulation coating plate on the heating wire;
    a far infrared ray diffusing pad disposed on the insulation coating plate, the pad having a plurality of crossed insertion parts formed by sewing double layers of textile materials in vertical and horizontal directions and filled with mineral particles therein; and
    a third cushion plate on the far infrared ray diffusing pad.

2. A far infrared ray diffusing mat, as defined in claim 1, wherein the heat reflecting plate and the water vein blocking plate are made out of an identical aluminum material.

3. A far infrared ray diffusing mat, as defined in claim 1, wherein the mineral particles comprise finely ground mica.

4. A far infrared ray diffusing mat, as defined in claim 1, wherein said heat reflecting plate and said water vein blocking plate are the same plate.

* * * * *